(12) United States Patent
Nielsen et al.

(10) Patent No.: US 10,213,563 B2
(45) Date of Patent: Feb. 26, 2019

(54) DRIVE MECHANISM FOR AN INJECTION DEVICE

(71) Applicant: Novo Nordisk A/S, Bagsvaerd (DK)

(72) Inventors: Christian Hoejris Nielsen, Copenhagen (DK); Ronan Carroll, Tisvildeleje (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/528,702

(22) PCT Filed: Nov. 23, 2015

(86) PCT No.: PCT/EP2015/077376
§ 371 (c)(1),
(2) Date: May 22, 2017

(87) PCT Pub. No.: WO2016/087251
PCT Pub. Date: Jun. 9, 2016

(65) Prior Publication Data
US 2017/0259010 A1    Sep. 14, 2017

(30) Foreign Application Priority Data

Dec. 5, 2014 (EP) .................................... 14196540

(51) Int. Cl.
*A61M 5/32* (2006.01)
(52) U.S. Cl.
CPC ........ *A61M 5/3243* (2013.01); *A61M 5/3257* (2013.01); *A61M 5/3245* (2013.01); *A61M 2005/3247* (2013.01)
(58) Field of Classification Search
CPC .............. A61M 5/3243; A61M 5/3257; A61M 5/3245; A61M 2005/3247; A61M 5/2033; A61M 5/20; A61M 5/3204; A61M 5/326; A61M 5/3287; A61M 5/3202; A61M 5/31551; A61M 5/3221; A61M 5/31501; A61M 5/31553; A61M 5/31568; A61M 5/3157; A61M 5/31586; A61M 5/24;
(Continued)

(56) References Cited

U.S. PATENT DOCUMENTS

2014/0094757 A1    4/2014   Mercer et al.

FOREIGN PATENT DOCUMENTS

| EP | 1819382 A1 | 8/2007 |
|----|-----------|--------|
| WO | 2004028598 A1 | 4/2004 |
| WO | 2006045528 A1 | 10/2005 |

(Continued)

OTHER PUBLICATIONS

WO2004/028598, Karlsson, date of publication: Apr. 8, 2004.*

*Primary Examiner* — Manuel A Mendez
(74) *Attorney, Agent, or Firm* — Wesley Nicolas

(57) ABSTRACT

The invention relates to an injection device for self-administration of doses of a liquid drug. The injection device carries a needle cannula (15) which is concealed by a telescopically movable shield (20). Further a stopping means (30) interconnects the shield with the helical rotatable scale sleeve (25) such that the shield can only be operated proximally when the scale sleeve is rotated away from its zero position. Once the scale sleeve returns to its zero position during expelling of the dose, the shield and the stopping means is allowed to slide distally and thus return to the locked position.

11 Claims, 2 Drawing Sheets

(58) Field of Classification Search
CPC .............. A61M 5/3232; A61M 5/3213; A61M 5/31541; A61M 5/31583; A61M 5/46
USPC ....................................................... 604/260
See application file for complete search history.

(56) References Cited

FOREIGN PATENT DOCUMENTS

| | | |
|---|---|---|
| WO | 2009040604 A1 | 4/2009 |
| WO | 2014064100 A1 | 5/2014 |
| WO | 2014082959 A1 | 6/2014 |

\* cited by examiner

DRIVE MECHANISM FOR AN INJECTION DEVICE

CROSS-REFERENCE TO RELATED APPLICATIONS

This application is a 35 U.S.C. § 371 National Stage of application of International Application PCT/EP2015/077376 (published as WO 2016/087251), filed Nov. 23, 2015, which claims priority to European Patent Application 141196540.0, filed Dec. 5, 2014; the contents of which are incorporated herein by reference.

THE TECHNICAL FIELD OF THE INVENTION

The invention relates to an injection device for self-administration of a liquid drug. The invention especially relates to such injection having a needle cannula which is concealed by a telescopic shield during injection.

DESCRIPTION OF RELATED ART

EP 1,819,382 discloses an example of a spring operated injection device in which a scale sleeve is rotated away from a zero position during dose setting and automatically returned to the initiate zero position during expelling of the set dose.

An injection device having a shielded needle cannula is known from WO 2014/064100, see especially FIGS. 17 and 18. The needle shield is moved from an extended position to a retracted position when the tip of the needle cannula is inserted into the skin of a user. A rotatable scale drum is provided for indicating to the user the size of the set dose. During dose setting this scale drume is rotated away from its zero position. Further a locking element is provided which moves, either rotational or proximally, to a position allowing the needle shield to move proximally when the scale drum is rotated away from its zero position. Following an injection, the scale drum automatically returns to its zero position where after the user removes the needle cannula from the skin. When no force is applied to the needle shield it returns to its extended position once again covering the tip of the needle cannula. Once the needle shield is re-positioned in its extended position, the locking element returns to its blocking position preventing the needle shield from moving proximally.

DESCRIPTION OF THE INVENTION

It is an object of the present invention to provide a locking element that is able to return to the initial position when the scale drum is positioned in its "zero" position.

The invention is defined in claim 1. Accordingly in one aspect the present invention relates to an injection device comprising the following elements:
A housing.
A dose setting element.
A needle cannula.
A needle shield.
A scale sleeve.
A stopping means.

The housing forms the outer shell and carries the dose setting element. In one example, the dose setting element is rotational mounted and able to be rotated in one direction to set the size of a dose to be injected and in an opposite direction to lower the size of the set dose.

The needle cannula is preferably permanently secured to the housing but could alternatively be exchangeable. The distal tip of the needle cannula is preferably grinded to allow easy penetration of the skin of a user during injection.

The needle shield is telescopically movable between a first position and a second position. In the first position the needle shield covers the distal tip of the needle cannula and in the second position the tip is exposed to perform an injection. The needle shield is urged into the first position by a resilient member such as a compression spring and preferably moved to the second position by being pressed against the skin of a user.

The scale sleeve is rotational in relation to the housing and is helical guided e.g. by being threaded to the housing. The scale sleeve carries indicia to inform the user of the selected dose and is moved away from a "zero" position during dose setting and returned to the same "zero" position during expelling of the set dose.

The "zero" position is often indicated on the scale sleeve by the cipher "0" or a similar indicia.

Further, a stopping means is provided which interconnects the needle shield and the scale sleeve. This stopping means engages the scale sleeve when the scale sleeve is in the "zero" position such that the needle shield is prevented from being moved in the proximal direction from the first position and into the second position but is allowed to be moved in the distal direction from the second position and into the first position.

The needle shield is thus prevented from being moved into the second position when no dose is dialled but allowed to move into the first position after the scale sleeve has returned to the zero position.

In one aspect, the injection device is a prefilled injection device provided with an End-of-Content mechanism i.e. a mechanism that prevents setting of a dose having a size surpassing the remaining injectable content of the cartridge. When an End-of-Content mechanism is provided, it will not be possible to rotate the scale sleeve once the content of the cartridge has been used because the E-o-C mechanism hinders rotation of the scale drum when the cartridge is empty. The needle shield is therefore permanently locked when the cartridge is empty.

Usually, as the liquid drug flow through the lumen of the needle cannula and into the skin, the scale sleeve rotates back to the zero position. In order for the entire dose to flow into the skin, the user has to wait 5 to 10 seconds before removing the tip of the needle cannula from the skin. In this waiting time, the scale sleeve has returned to zero. It must therefore be possible for the locking means and consequently for the needle shield to return to the first position after the scale sleeve has returned to the "zero" position.

As implied above, in one example the stopping means and the needle shield move together at least in an axial direction. In one example, the needle shield and the stopping means could be moulded as one unitary element, such that the needle shield carries the stopping means. However, both the needle shield and the stopping means could alternatively be an assembly made up from several parts.

The stopping means (or stopping assembly) preferably comprises an arm which extends proximally to engage the scale sleeve.

The stopping means (or stopping assembly) further comprises a recession. The recession is preferably formed as an indentation in the stopping means.

In one example, the recession is provided in the axial extending arm. However, the stopping means is not necessarily provided with an arm and should an arm be present, the presence of a plurality of arms could easily be foreseen.

The arm or arms extend axially and preferably lies in the same radial plane as the scale sleeve. The arm thus has an outer surface pointing radially outwardly and an inner surface pointing radially towards a centre line of the injection device. These two outer surfaces are connected by two peripheral sides.

The recession is preferably either provided in a peripheral side of the arm or in the inner surface of the arm. Alternatively the recession can be provided both in the peripheral side and in the bottom of the arm.

In one example of the invention, the scale sleeve carrying the indicia indicating the size of the set dose is distally provided with a peripheral extending extension which in the figures is depicted as a protrusion but could have any desired shape. By peripheral is here meant that the extension extend in a direction along the inner periphery of the housing. The extension is thus a continuation of the outer surface of the scale sleeve.

Following an injection, when the scale sleeve returns to the "zero" position, the peripheral extending extension engages the recession which allow the needle shield and the stopping means to slide axially from the second position and into the first position with the scale sleeve remaining in the zero position.

In a further embodiment the arm of the stopping means is formed flexible such that it can move slightly in the peripheral plane relatively to the scale sleeve thus allowing the recession to slide by the scale sleeve. When the recession is located on the inner surface of the arm, the arm preferably flexes in the radial plane.

Alternatively, the stopping means can be rotational mounted relatively to the housing such that the stopping means can deflect during passage of the peripheral protrusion of the scale sleeve. The stopping means are preferably rotated into position by a torsion spring. In a further embodiment, the torsion spring is the same spring which urges the stopping means in the distal direction. The spring thus provides both an axial force and a torsional force when twisted.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

"Scale drum or scale sleeve" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols.

These symbols are preferably, but not exclusively, Arabian numbers from "0" to "9". In a traditional injection pen configuration the indicia is viewable through a window provided in the housing.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g.

in the form of a button on, e.g. on the proximal end, of the injection device to release—fully or partially—the force accumulated in the spring when carrying out the injection.

The term "Permanently connected" as used in this description is intended to mean that the parts, which in this application is embodied as a cartridge and a needle assembly, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 1:
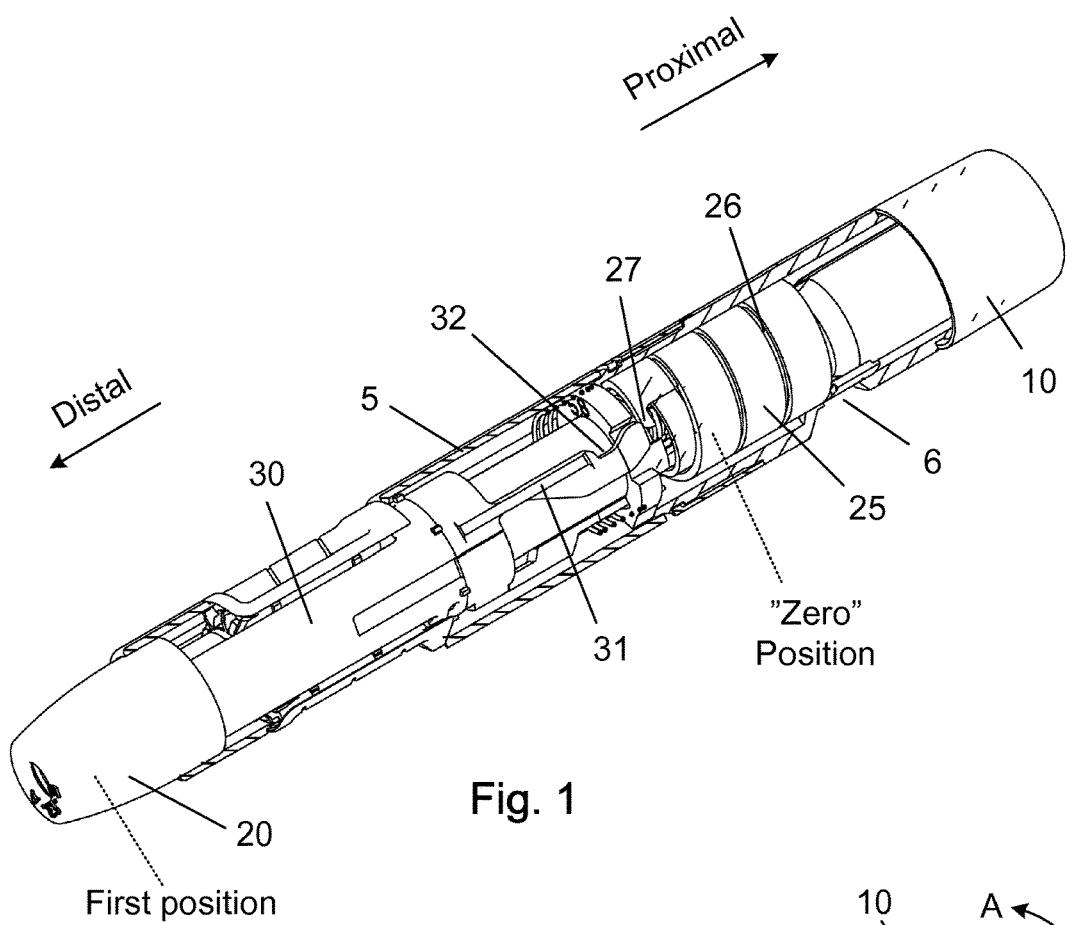
FIG. 1 show a perspective view of the injection device with needle shield extending in the first position, and the scale drum in the "zero" position.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Distal and proximal are meant to be along an axial orientation extending along the longitudinal axis of the disclosed injection device and is further indicated in FIG. 1, FIGS. 1 to 4 discloses the injection device according to a first embodiment. The injection device comprises the following components:

A housing 5.
A dose dial element 10
A needle cannula 15.
A needle shield 20
A scale sleeve 25

The housing 5 forms the outer shell carrying the cartridge containing the liquid drug and is usually held in the hand of the user when performing an injection.

The dose dial element 10 is provided proximally on the housing 5 and is usually rotational secured to the housing 5. The user rotates this dose dial element 10 in order to set the size of the dose to be injected. This rotation usually strains a not-shown torsion spring which again delivers the force needed to perform the injection. This is e.g. shown in EP 1,819,382.

The needle cannula 15 is preferably permanent secured to the injection device and has a sharp tip 16 which penetrates the skin of the user during injection.

The needle cannula 15 is hidden behind a needle shield 20 between injections. This needle shield 20 is usually urged in the distal direction by a resilient element positioned between the housing 5 and the needle shield 20.

The scale sleeve 25 has a helical groove or thread 26 which is engaged in a similar, male thread formed on the inside surface of the housing. However, the thread 26 of the scale sleeve 25 could alternatively be provided on the inside of the scale sleeve 25 and the thread of the housing 5 could be provided as an outwardly pointing thread on an internal tower forming part of the housing 5. In either case, the thread in the housing 5 needs only be a segment of a thread.

When a user wants to set a dose, the housing 5 is held in one hand and the dose dial element 10 is rotated using the other hand. This rotation is indicated with the arrow "A" in FIG. 2.

During dose setting, the scale drum 25 rotates and moves helical inside the housing 5. Usually indicia are provided on the scale drum 25 and preferably in a helical row such that when the scale drum 25 is rotated helically these indicia pass by a window 6 in the housing 5 one at the time thereby displaying the size of the set dose.

As disclosed in FIG. 1, when no dose is set, the scale sleeve 25 is in the "zero" position usually with the number "0" (or similar indicia) showing in the window 6.

Figure 2:
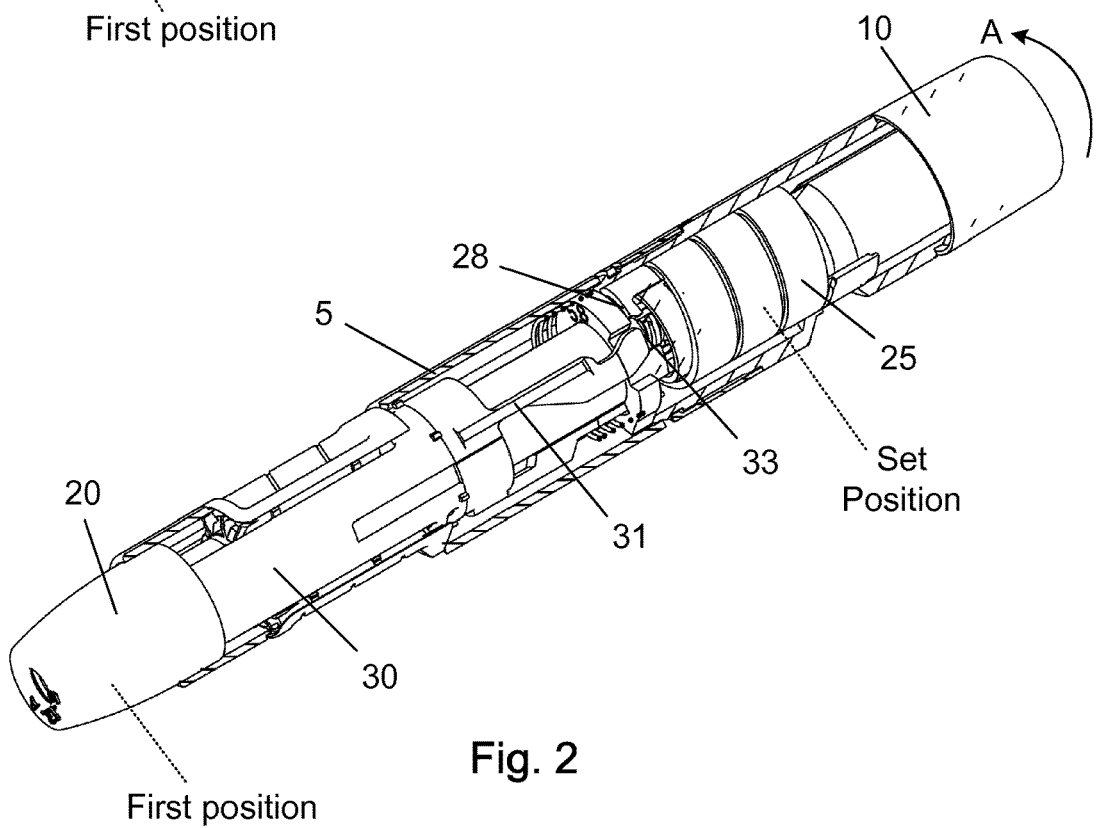
FIG. 2 show a perspective view of the injection device with the needle shield extending in the first position, and the scale drum dialled away from the "zero" position.

In FIG. 2, during dose dialling, the scale sleeve 25 rotates away from the "zero" position and the indicia provided on the scale sleeve 25 rotate pass the window 6.

Figure 3:
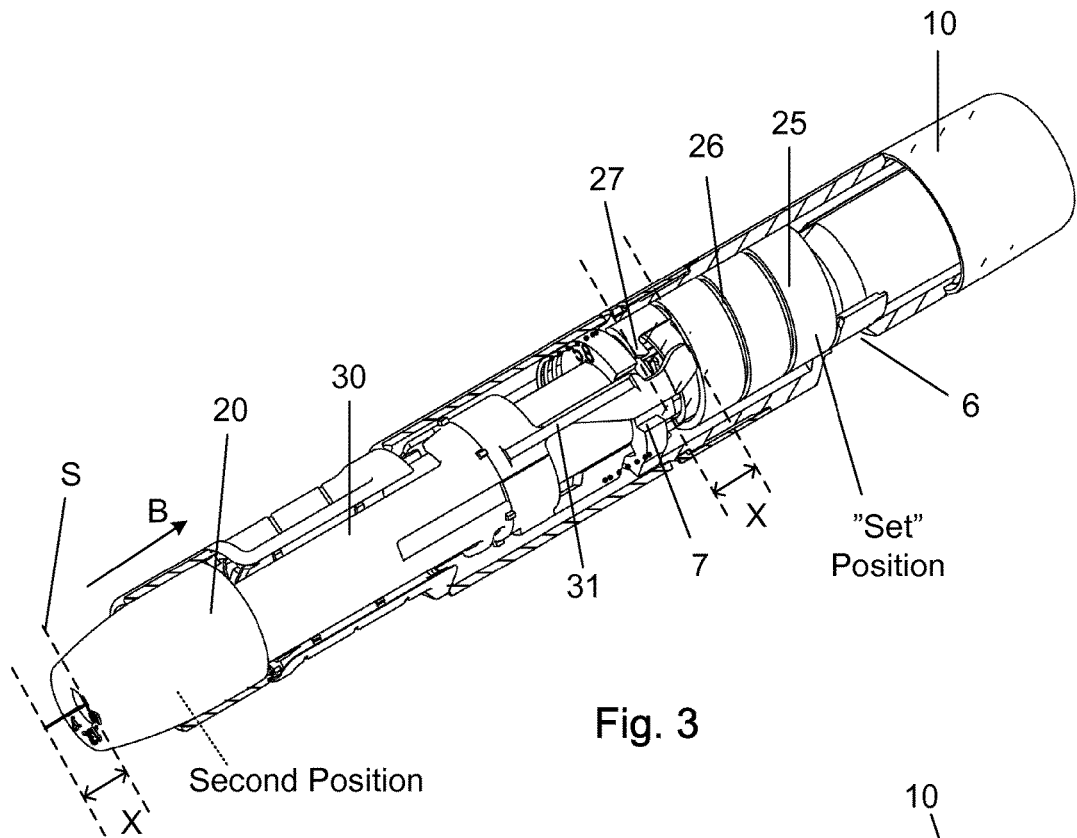
FIG. 3 show a perspective view of the injection device with the needle shield retracted to the second position, and the scale drum dialled away from the "zero" position.

When injecting as disclosed in FIG. 3, the scale sleeve 25 rotate back towards the "zero" position and the indicia pass by the window 6 in the opposition order.

Figure 4:
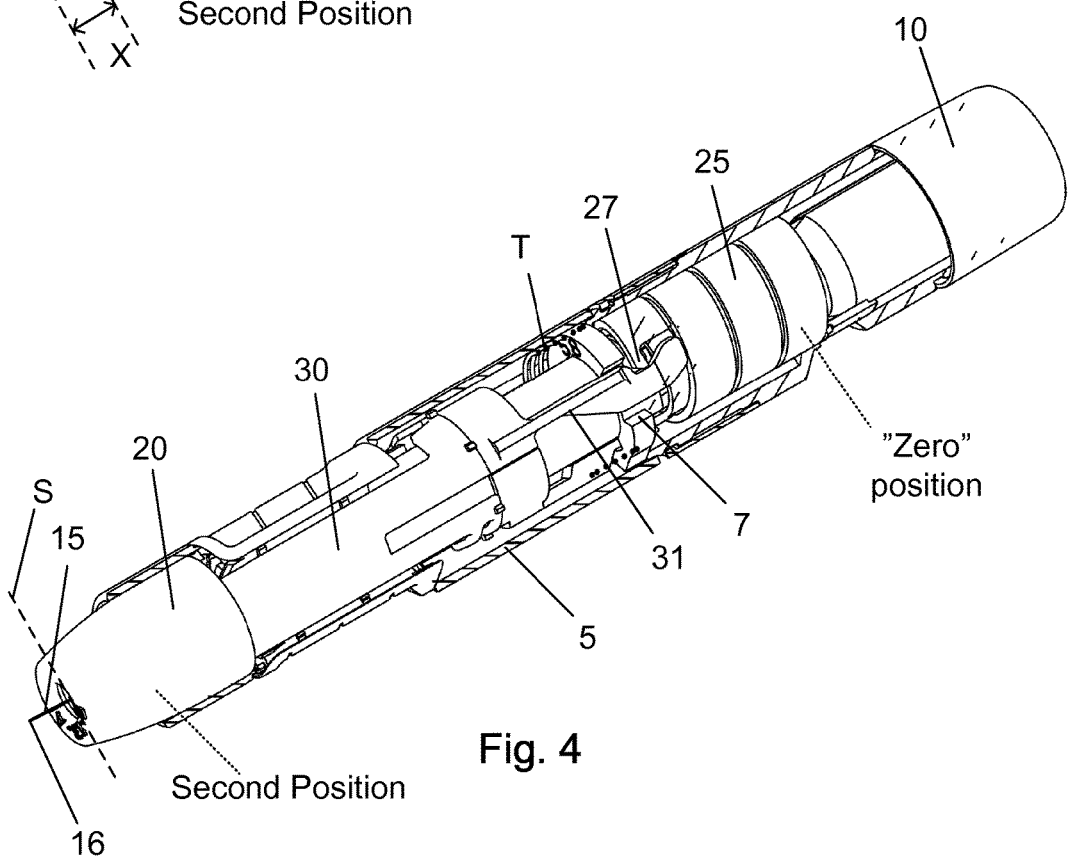
FIG. 4 show a perspective view of the injection device with the needle shield retracted to the second position, and the scale drum returned to the "zero" position.

Once the injection is over as depicted in FIG. 4, the scale sleeve 25 has returned to its initiate "zero" position, and the number "0" (or similar indicia) is again shown in the window 6.

FIG. 1 depicts the injection device prior to dose setting with the scale drum 25 resting in the "zero" position and the number "0" (or similar indicia) therefore being displayed in the window 6.

The scale sleeve 25 is distally provided with a peripheral extending extension 27 e.g. in the form of a protrusion. This extension or protrusion 27 lies peripheral to the inside surface of the housing 5. Distally this peripheral extending extension 27 is provided with a distal side surface 28.

Further, a stopping means 30 is provided between the needle shield 20 and the scale sleeve 25. The stopping means 30 can in one embodiment be provided with an axial extending arm 31. The stopping means 30 can in one example be integral with the needle shield 20 or it can alternatively be a separate part inserted between the needle shield 20 and the scale sleeve 25.

The proximal extending arm 31, which extends from the stopping element 30 preferably has a recession 32 on the peripheral pointing towards the peripheral extending protrusion 27 of the scale sleeve 25. Most proximally this arm 31 has an end surface 33 which lies in the same peripheral plane as the scale sleeve 25.

As best seen in FIG. 1, when no dose has been set, i.e. when the scale sleeve 25 is positioned in the "zero" position, the needle shield 20 is prevented from telescoping in the proximal direction by the engagement between the arm 31 and the scale sleeve 25. The stopping means 30 distally engages the needle shield 20 (or the stopping means 30 is integral with the needle shield 20). Proximally the stopping means 30 preferably via the arm 31 engages the scale sleeve 25. The engagement with the scale sleeve 25 occurs as an abutment between the distal surface 28 of the extending extension 27 of the scale sleeve 25 and the proximal surface 33 of the arm 31.

When a user sets a dose as illustrated in FIG. 2, the dose dial element 10 is rotated (arrow "A") which in turn also rotates the scale sleeve 25 to move helically away from the "zero" position. Once the scale sleeve 25 is rotated, the peripheral extending protrusion 27 is also rotated away from the engagement with the proximal end surface 33 of the arm 31. The arm 31 and thus the stopping means 30 are here after free to move proximally. Since the scale sleeve 25 rotates helically away the free space into which the arm 31 can move grows rapidly as the dose is being set.

At the start of the injection, the user presses the distal surface of the needle shield 20 against the skin "S" as indicated by the arrow "B" in FIG. 3. This presses the needle shield 20 and the stopping means 30 in the proximal direction. Since the scale sleeve 25 has been rotated proximally, sufficient space is available to move the stopping means 30 and the thus the arm 31 proximally.

The injection is thereafter done either manually by the user pressing an injection button or automatically by an electric motor or by a spring drive. When the injection is done automatically, the proximal movement of the needle shield 20 can be made to trigger the commencement of the injection.

As the injection is carried out and the liquid drug flow into the body of the user via the lumen of the needle cannula 15, the scale sleeve 25 graduately returns to the initiate "zero" position in a helical movement.

As indicated in FIG. 3, the needle cannula 15 is inserted into the skin ("S") into the depth "X". When injecting a modern insulin product, this depth ("X") is usually 3 to 8 mm. The needle shield 20 is thus retracted the same distance ("X"). As a result of this, the arm 31 of the stopping means 30 is also telescoped a distance "X" from the initiate position.

When the transfer of liquid drug has ended, the scale sleeve 25 has returned to the initiate "zero" position as disclosed in FIG. 4. In FIG. 4, the needle cannula 15 is still inserted into the skin ("S") of the user. When the scale sleeve 25 returns to the "zero" position, the peripheral extending protrusion 27 will enter into the recession 32 in the arm 30. In FIG. 4 the recession 32 is disclosed as being positioned on the peripheral side of the arm 31 but the recession 32 could also be provided on the bottom surface of the arm 31 i.e. the part of the arm 31 pointing towards the centre line of the injection device. It could also be a combination of the two. The main point is that the arm 31 and the stopping means 30 must be able to slide distally into the first position with the scale sleeve 25 in the "zero" position. This could also be obtained by having flexibility build into the arm 31.

Further, the stopping means 30 could be allowed to rotate a few degrees during returning of the needle shield 20 e.g. against the force of a resilient element that would bring the stopping means 30 back to its initial rotational position once it has passed the peripheral extending extension 27 on the scale sleeve 25. The resilient element could e.g. be a torsion spring. In one example the spring urging the needle shield 20 in the distal direction could be a combined compression spring and torsion spring encompassed between the stopping means 30 and the housing 5. Such spring is explanatory disclosed in the FIGS. 1 to 4 with the reference "T". This spring could simultaneously urge the stopping means 30 in a distal direction and torsional rotate the stopping means 30 into its rotational position, e.g. determined by a guiding arrangement 7 secured in the housing 5. In such case the needle shield 20 and the stopping means 30 are preferably made as independent parts such that the needle shield 20 which is in contact with skin ("S") of the user during injection is only moved axially.

When the user removes the needle cannula 15 from the skin ("S"), the needle shield 20 slides into the locked position depicted in FIG. 1 and the needle shield 20 is thus prevented from being moved in the proximal direction.

Some preferred embodiments have been shown in the foregoing, but it should be stressed that the invention is not limited to these, but may be embodied in other ways within the subject matter defined in the following claims.

The invention claimed is:

1. An injection device for self-administration of settable doses of a liquid drug comprising:
    a housing grippable by a user,
    a dose setting element by which the size of the dose is set,
    a needle cannula having a distal tip for penetrating the skin of the user during injection,
    a needle shield which is telescopically movable in a proximal direction from a first position to a second position and in a distal direction from the second position back to the first position by a resilient element, and wherein the needle shield in the first position is extended distally to cover at least the distal tip of the needle cannula and in the second position is retracted proximally to expose the distal tip of the needle cannula,
    a rotatable scale sleeve indicating the size of the set dose which scale sleeve is helically guided relatively to the housing, the scale sleeve being helically moved away from an initial "zero" position during dose setting and helically returned to the same initial "zero" position during dose injection,
    wherein a stopping structure interconnects the needle shield and the scale sleeve, which stopping structure engages the scale sleeve when the scale sleeve is in the "zero" position such that the needle shield is prevented from being moved in the proximal direction from the first position and into the second position but is allowed to be moved in the distal direction from the second position and into the first position, and wherein the needle shield carries the stopping structure such that the needle shield and the stopping structure move together at least in the axially direction.

2. An injection device according to claim 1, wherein the stopping structure comprises a proximally extending arm.

3. An injection device according to claim 1, wherein the stopping structure comprises a recession.

4. An injection device according to claim 3, wherein the recession is provided on the axial extending arm.

5. An injection device according to claim 4, wherein the recession is provided in a peripheral side of the arm.

6. An injection device according to claim 4, wherein the recession is provided in a bottom surface of the arm.

7. An injection device according to claim 1, wherein the scale sleeve distally comprises a peripheral extending protrusion.

8. An injection device according to claim 7, wherein the peripheral extending protrusion engages the recession when the scale sleeve is in the "zero" position and the needle shield is the second position.

9. An injection device according to claim 8, wherein the engagement allows the needle shield and the stopping structure to slide axially from the second position and into the first position with the scale sleeve remaining in the zero position.

10. An injection device according to claim 1, wherein the stopping structure is flexible.

11. An injection device according to claim 1, wherein the stopping structure is rotationally mounted relatively to the housing.

* * * * *